(12) United States Patent  
Kim

(10) Patent No.: US 9,116,114 B2  
(45) Date of Patent: Aug. 25, 2015

(54) ELECTROCHEMICAL BIOSENSOR ELECTRODE STRIP AND A FABRICATION METHOD THEREOF COMPRISING A TITANIUM METAL LAYER ON A CARBON LAYER AS THE ELECTRODE MATERIAL

(75) Inventor: Seok-Hun Kim, Seoul (KR)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 229 days.

(21) Appl. No.: 13/884,337

(22) PCT Filed: Oct. 26, 2011

(86) PCT No.: PCT/US2011/057828  
§ 371 (c)(1),  
(2), (4) Date: May 9, 2013

(87) PCT Pub. No.: WO2012/064509  
PCT Pub. Date: May 18, 2012

(65) Prior Publication Data  
US 2013/0228461 A1    Sep. 5, 2013

(30) Foreign Application Priority Data

Nov. 9, 2010   (KR) .................. 10-2010-0111127

(51) Int. Cl.  
*G01N 27/327*    (2006.01)  
*G01N 27/30*     (2006.01)

(52) U.S. Cl.  
CPC .......... *G01N 27/327* (2013.01); *G01N 27/3272* (2013.01); *G01N 27/308* (2013.01)

(58) Field of Classification Search  
CPC .......... C12Q 1/00; C12Q 1/54; G01N 27/327; G01N 27/3272; A61B 5/150274; B32B 38/04; C23C 28/00  
See application file for complete search history.

(56) References Cited

U.S. PATENT DOCUMENTS

2009/0155800 A1    6/2009  Hong

FOREIGN PATENT DOCUMENTS

| CN | 101520428 | 9/2009 |
|---|---|---|
| WO | WO 2010-123802 | 10/2010 |

OTHER PUBLICATIONS

Yang, Amperometric nitrite sensor based on hemoglobin/colloidal gold nanoparticles immobilized on a glassy carbon electrode by a titania sol-gel film, Anal Bioanal Chem (2005), 382: pp. 44-50.

Zhao, Hemoglobin/colloidal silver nanoparticles immobilized in titania sol-gel film on glassy carbon electrode: Direct electrochemistry and electrocatalysis, ScienceDirect, Bioelectrochemistry, 2006, vol. 69, No. 1, pp. 10-15.

*Primary Examiner* — Jennifer Dieterle  
(74) *Attorney, Agent, or Firm* — Clifton F. Richardson

(57) ABSTRACT

The present invention relates to an electrochemical biosensor electrode strip fabricated by forming a carbon layer on a non-conductive substrate made of polymer material, forming a metal layer containing titanium thereon, and performing patterning.

13 Claims, 4 Drawing Sheets

ELECTROCHEMICAL BIOSENSOR ELECTRODE STRIP AND A FABRICATION METHOD THEREOF COMPRISING A TITANIUM METAL LAYER ON A CARBON LAYER AS THE ELECTRODE MATERIAL

TECHNICAL FIELD

The present invention relates to an electrochemical biosensor electrode strip, which can be fabricated at low cost and has excellent performance, and a method of fabricating the same. More particularly, the present invention relates to an electrode strip of an electrochemical biosensor test strip for quantitatively analyzing specific substance in a biological sample, for example, glucose in blood, and a method of fabricating the same.

BACKGROUND

Recently, in the medicament field, an electrochemical biosensor has been frequently used to analyze biological samples including blood. Especially, an electrochemical biosensor using an enzyme is being widely used since its application is easy, it has high measurement sensitivity, and results can be quickly obtained.

As to examples of such an electrochemical biosensor, there is a glucose measuring biosensor. The operation mechanism thereof will be described.

As to a glucose measuring biosensor, a certain electrode is formed, and then a glucose oxidase, as an analysis reagent, is immobilized onto part of the electrode to form a reaction layer. When a blood sample is introduced onto the reaction layer, glucose in the blood is oxidized by the glucose oxidase, and the glucose oxidase is reduced. An electron acceptor oxidizes the glucose oxidase and is reduced. The reduced electron acceptor loses its electrons on the electrode surface, to which predetermined voltage has been applied, and is electrochemically re-oxidized. Since glucose concentration in the blood sample is in proportion to an amount of current generated during the oxidization of the electron acceptor, glucose concentration can be measured by measuring the current amount.

By using this electrochemical biosensor, it is possible to measure uric acid and protein, in addition to glucose, in blood. Furthermore, it is possible to measure enzyme activity of GOT (Glutamate-Oxaloacetate Transaminase) or GPT (Glutamate-Pyruvate Transaminase) for DNA and liver function tests.

Herein, the biosensor is divided into an identification portion for identifying an object to be measured and a conversion portion for performing conversion into an electrical signal. For the identification portion, a biological material is used, whereby when the biological material identifies an object to be measured, a chemical or physical change occurs. The conversion portion converts the change into an electrical signal and is generally called as a biosensor electrode.

As to a method of fabricating this biosensor electrode, there is a silk printing method. A silk printing method is a printing method using platinum, carbon, or silver/silver chloride ink, which requires low equipment cost but has a problem since adjusting resistance variation to fabricate a sensor electrode requiring reproducibility is difficult.

As to another method of fabricating the biosensor electrode, there is a vacuum deposition or sputtering method using a patterned mask and precious metals. According to this method, a patterned mask is deposited on a substrate, and vacuum deposition or sputtering using precious metals is performed to form electrode patterns. However, this method is problematic since costs are expensive due to use of precious metals, and there is difficulty in recovering precious metals.

In addition, a conventional sputtering method performs sputtering by using a patterned mask. That is, since sheet-type sputtering should be performed, and long time is required to perform the sputtering, production efficiency is low.

Meanwhile, in order to fabricate a biosensor electrode, metal patterning technology, which has been conventionally used to fabricate a printed circuit board (PCB), may be applied to fabrication of an electrochemical biosensor electrode for quantifying specific substance in a biological sample such as blood.

However, in conventional PCB fabrication, an electrode is fabricated by using copper, etc. Laminating metal on the copper substrate causes a non-uniformed and lumpy surface so that the sample flows into the lower layer of the copper, and thereby generating an electrical signal disturbing a measurement value. Thus, this method was not suitable for application to fabrication of a biosensor electrode. Moreover, since copper or nickel used in the PCB is electroactive, namely unstable, at voltage generally used in an electrochemical biosensor, it was not suitable as an electrode material for an electrochemical biosensor.

An electrode material for an electrochemical biosensor should be a conductive material non-active to an enzyme. A conductive material non-active to an enzyme mostly include a semiconductor material, etc., such as carbon, platinum, palladium, gold, and indium on which a titanium oxide is doped. These materials are deposited generally by CVD (Chemical Vapor Deposition), PVD (Physical Vapor Deposition), and screen printing methods. These methods require a precise technique to achieve an accurate size and performance of an electrode. However, despite that the non-active materials other than carbon have excellent electrical characteristics, mass production thereof is difficult since they are highly expensive. Thus, in order to reduce electric resistance, depositing carbon thick by using a screen printing method is generally adopted. However, since the screen printing method using a carbon ink results in low hardness and non-uniform thickness, it has many defects such as irregularity of electric resistance, generation of carbon particles, and complicated processes.

As such, a technique of sputtering and depositing a chrome layer and a nickel layer on a substrate may be considered. However, since chrome is a metal having activity to an enzyme, in order to reduce the risk of reaction of chrome with an enzyme after LASER etching, a technique of depositing a carbon layer and sputtering a titanium layer, which exhibits a non-active characteristic to an enzyme and has high conductivity, is hereby introduced.

SUMMARY

At least one embodiments of the present invention provides an improved electrochemical biosensor electrode, which can solve the problems in conventional technology that have been described, and a method of fabricating the same.

An object of at least one embodiment of the present invention is to provide an electrochemical biosensor electrode and a method of fabricating the same, which can reduce fabrication time and cost by using fewer components and simplifying fabrication processes.

Another object of at least one embodiment of the present invention is to provide an electrochemical biosensor electrode, which has a uniformed surface, can be patterned to have a desired shape so that it can be appropriately transformed as required, and has an excellent detection property, and a method of fabricating the same.

At least one embodiments of the present invention provides an electrode strip to be used for an electrochemical biosensor, which requires low fabrication cost and has excellent performance.

The electrochemical biosensor electrode strip of at least one embodiments of the present invention comprises a strip-shaped non-conductive substrate, and at least two electrodes formed on the substrate and operating as a working electrode and a reference electrode, wherein the electrodes comprise a carbon layer and a metal layer, in which the carbon layer is formed on the substrate, and the metal layer is formed on the carbon layer, and the metal layer contains titanium.

At least one embodiments of the present invention also provides a method of fabricating the electrochemical biosensor electrode strip. The method of fabricating the electrochemical biosensor electrode strip according to an aspect of the present invention comprises: a step of preparing a non-conductive substrate; a step of forming a carbon layer on the substrate; a step of forming a metal layer containing titanium on the formed carbon layer to form a conductive layer consisting of the carbon layer and the metal layer; and a step of partially etching the conductive layer to pattern an electrode shape.

According to at least one embodiments of the present invention, since an electrode having a uniform surface is formed, the detection accuracy can be improved. In addition, since a carbon layer and a metal layer containing titanium on a non-conductive film can be sputtered through continuous processes in an identical chamber, fabrication processes are convenient, and mass production is possible.

DETAILED DESCRIPTION

Figure 1:
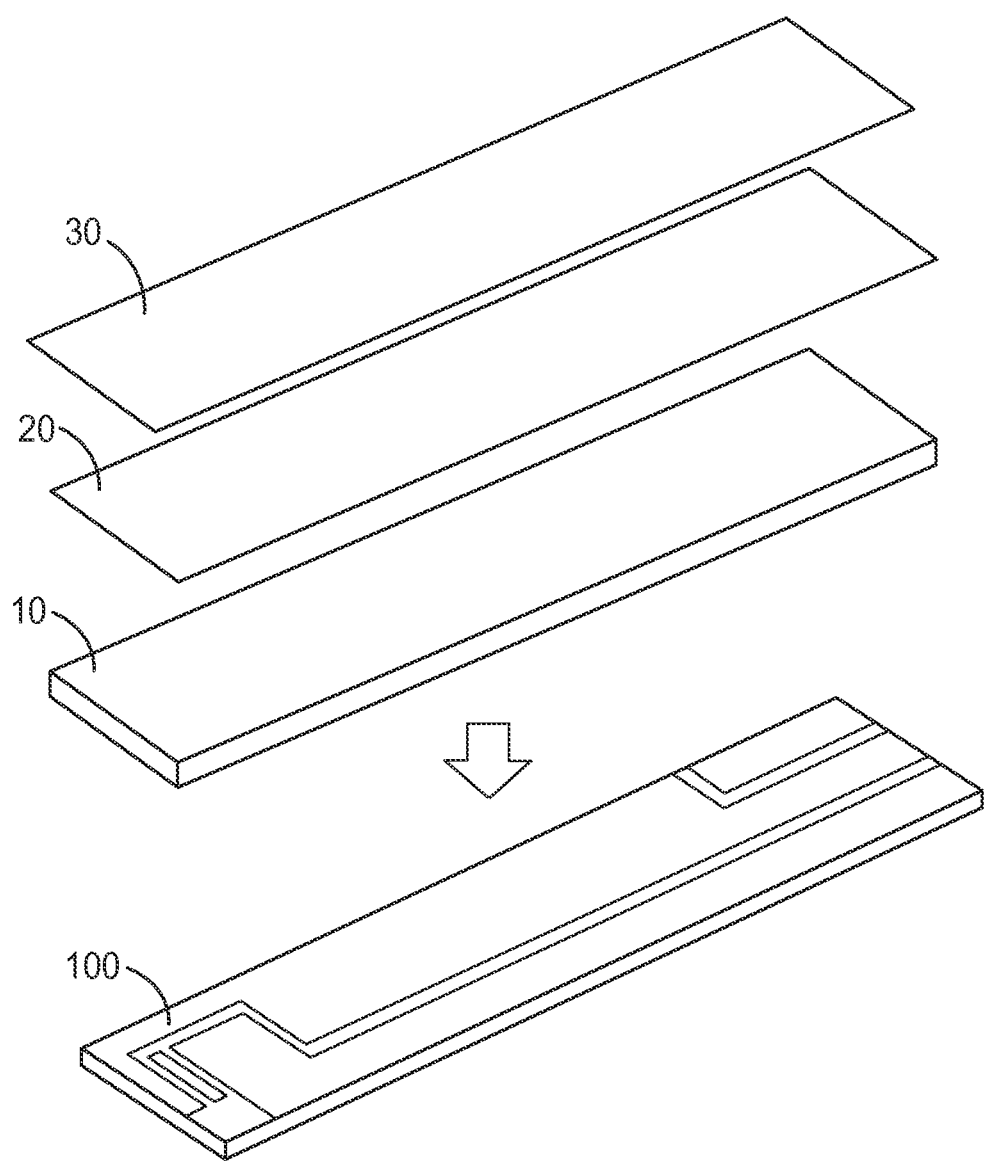
FIG. 1 schematically illustrates fabrication processes of one embodiment of the electrochemical biosensor electrode strip according to an aspect of the present invention.

The electrochemical biosensor electrode strip and the method of fabricating the same according to at least one embodiments of the present invention will be described in more detail with reference to the accompanying drawings. First of all, terms and words used in this specification and the appended claims should not be defined by general or dictionary meanings and should be defined by meanings and concepts in compliance with the technical idea of the present invention without departing from the principle that the inventor may appropriately define concepts of words in order to describe the inventor's invention in best modes.

The constitution illustrated in the drawings and the embodiments described in this specification are merely the most preferable embodiment of the present invention and do not represent the entire technical idea of the present invention. Thus, it should be understood that there may be various equivalents and modified embodiments, which can substitute for the embodiments described herein, at the time of filing of the application for the present invention.

The electrochemical biosensor electrode strip (100) of an embodiment of the present invention comprises a strip-shaped non-conductive substrate (10), and at least two electrodes formed on the substrate and operating as a working electrode (101) and a reference electrode (102), wherein the electrodes comprise a carbon layer (20) and a metal layer (30), in which the carbon layer (20) is formed on the substrate (10) (see FIG. 1), and the metal layer (30) is formed on the carbon layer (20), and the metal layer (30) contains titanium.

Generally, since titanium has high strength, it is difficult to uniformly sputter it on a substrate. However, by first sputtering a carbon layer on a substrate and then sputtering a metal layer containing titanium on the carbon layer, surface roughness can be made uniform, and constant electric resistance can be maintained. That is, fabricating a more reliable sensor is possible.

Figure 2:
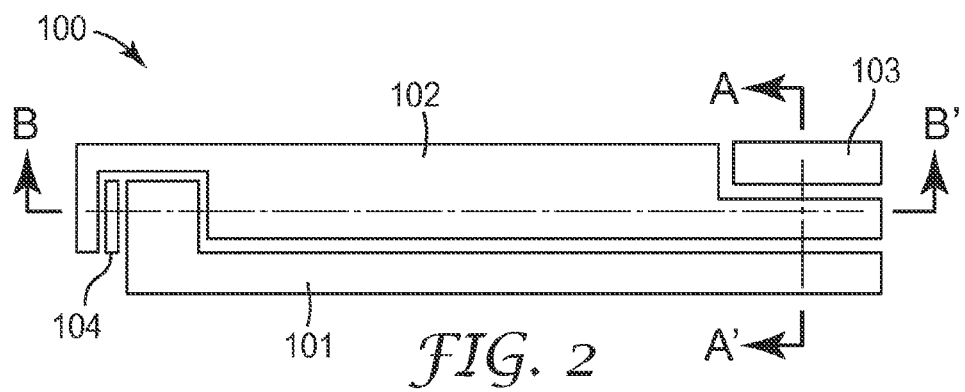
FIG. 2 is a top view showing electrode disposition of an electrode strip fabricated in FIG. 1.
Figure 3:
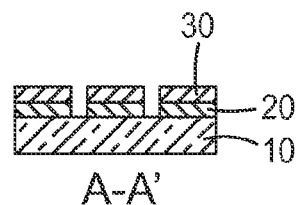
FIG. 3 is a sectional view of an electrode strip fabricated in FIG. 1, which is cut along the A-A' line in FIG. 2.
Figure 4:
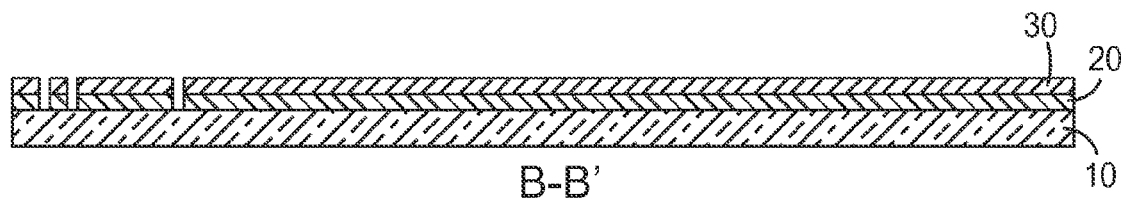
FIG. 4 is a sectional view of an electrode strip fabricated in FIG. 1, which is cut along the B-B' line in FIG. 2.

FIG. 2 is a top view showing electrode disposition of the electrochemical biosensor electrode strip according to one embodiment of the present invention. FIG. 3 shows a view cut along the A-A' line in FIG. 2. FIG. 4 shows a view cut along the B-B' line in FIG. 2.

According to one embodiment of the present invention, the carbon layer (20) and the metal layer (30) can be formed by sputtering. Forming a thin film having a uniform thickness through the sputtering is possible.

According to one embodiment of the present invention, the thickness of the carbon layer (20) may be 1000 Å~1500 Å, and the thickness of the metal layer (30) may be 500 Å~-1500 Å. The thickness can be adjusted in consideration of fabrication convenience and electrical characteristics, etc.

In the present invention, the metal layer (30) forming the electrode is a metal layer containing titanium as a main material.

According to one embodiment of the present invention, an auxiliary electrode (104) may be further formed between the working electrode (101) and the reference electrode (102). In this structure, a biological sample to be measured may be applied to the portion in which the auxiliary electrode is formed.

In other words, when the electrochemical biosensor electrode strip (100) of the present invention is applied to a biosensor, a reagent, etc., which can react with a biological sample to be measured, is disposed in the portion, in which the working electrode (101) and the reference electrode (102) are adjacent to each other. The reagent may be disposed in the portion, in which the auxiliary electrode (104) is disposed.

For example, when the electrochemical biosensor electrode strip of at least one embodiment of the present invention is used for a kit which measures glucose in blood, the portion, in which the auxiliary electrode (104) is disposed, may be a reaction portion. On the reaction portion, a reagent, such as a reagent mainly containing hydrogel and glucose oxidase (hereinafter referred to as a "GO"), may be disposed. Herein, when a blood sample is applied to the reaction portion, glucose contained in the blood sample is oxidized by enzymatic reaction with GO, and GO is reduced. The reduced GO is re-oxidized through reaction with an electron acceptor, and the oxidized GO reacts with another glucose. The reduced electron acceptor moves onto the electrode surface, to which voltage is applied, and loses its electrons so that it is electrochemically re-oxidized and continues to participate in the reaction. Since current generated in the oxidization process of the electron acceptor is in proportion to concentration of glucose in blood, glucose concentration in blood can be quantitatively measured by measuring an amount of current between the working electrode (101) and the reference electrode (102). Meanwhile, the auxiliary electrode (104) may perform a role of facilitating the electricity flow between the working electrode (101) and the reference electrode (102) and function as an indicator for indicating the reaction portion.

Also, in consideration of the case where the electrochemical biosensor electrode strip is used to be inserted into a tester, a recognition electrode (103) for confirming whether the electrode strip is properly inserted into a tester may be further provided. For example, if the electrode strip is inserted into a tester, the tester may be configured in such a manner that the recognition electrode (103) is electrically connected to a sensing circuit separately provided in the tester.

According to one embodiment of the present invention, for the non-conductive substrate (10), an insulating polymer film may be used. There is no limitation to the insulating polymer film if it has an insulating property. Examples of the insulating polymer film include a polyethylene telephthalate (PET) film, an epoxy resin film, a phenolic resin film, a polyethylene film, a polyvinyl chloride film, a polyester film, a polycarbonate film, a polystylene film, and a polyimide film, etc. Types of the insulating polymer film are not limited to these films.

According to one embodiment of the present invention, a process of pre-baking a non-conductive substrate may be performed, prior to a process of depositing a carbon, in order to remove the moisture that the substrate inherently has.

The present invention also provides a method of fabricating an electrochemical biosensor electrode strip comprising: a step of preparing a non-conductive substrate; a step of forming a carbon layer on the substrate; a step of forming a metal layer on the formed carbon layer to form a conductive layer consisting of the metal layer and the carbon layer; and a step of partially etching the conductive layer to pattern an electrode shape.

One embodiment of the present invention uses a large and wide substrate, on which a plurality of electrode patterns are formed. The substrate is cut along with each of the electrode patterns so that respective independent electrodes can be fabricated.

According to one embodiment of the present invention, the carbon layer and the metal layer containing titanium can be formed by sputtering.

According to one embodiment of the present invention, the carbon layer and the metal layer are sputtered to form a conductive layer consisting of the carbon layer and the metal layer. Thereafter, electrode patterns are formed through etching. For the etching, LASER etching may be applied. Even after the LASER etching, the electrode fabricated by the fabrication method according to an aspect of the present invention can have excellent properties since the carbon layer therein has no reactivity with an enzyme.

If the LASER etching is used to form electrode patterns, micro-shaped electrode patterns can be conveniently formed. Unlike some etching methods using a solvent, the LASER etching does not have the potential to cause environmental pollution resulting from the solvent.

According to one embodiment of the present invention, after the entire surface of the substrate is sputtered to form a conductive layer, LASER etching is performed to form electrode patterns. Thus, there is no need to use a patterned mask during sputtering.

That is, if LASER etching is applied in the present invention, a direct sputtering method to sputter the entire surface of the substrate at one time can be applied. In case of direct sputtering, there is no need to use a patterned mask during sputtering. Further, since a roll to roll process is possible, the sputtering process is simplified, and thereby reduces process time. As a result, production efficiency improves.

In addition, since patterns can be easily formed by LASER etching, mass production can be easily achieved.

The working electrode (101) and the reference electrode (102) can be formed by the etching, and furthermore, at least one additional electrode selected from the auxiliary electrode (104) and the recognition electrode (103) may be formed.

The electrochemical biosensor electrode strip according to an aspect of the present invention can be fabricated as illustrated in FIG. 1.

Figure 5:
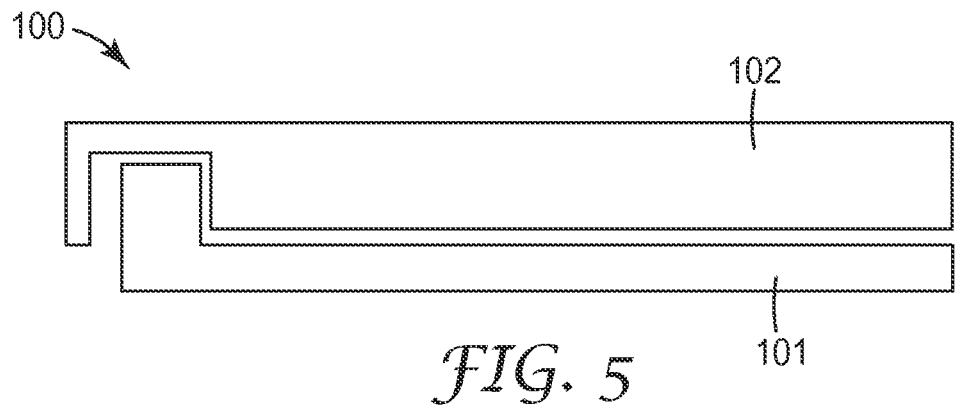
FIGS. 5 to 7 show other embodiments of the electrochemical biosensor electrode strip according to the present invention.
Figure 6:
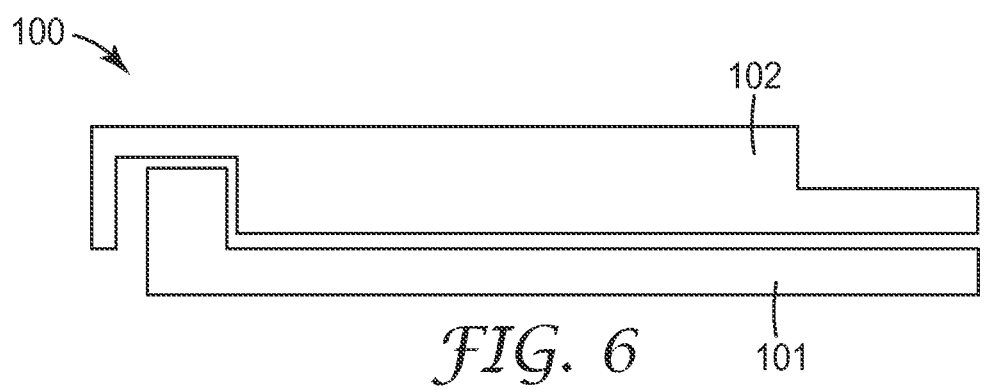
Figure 7:
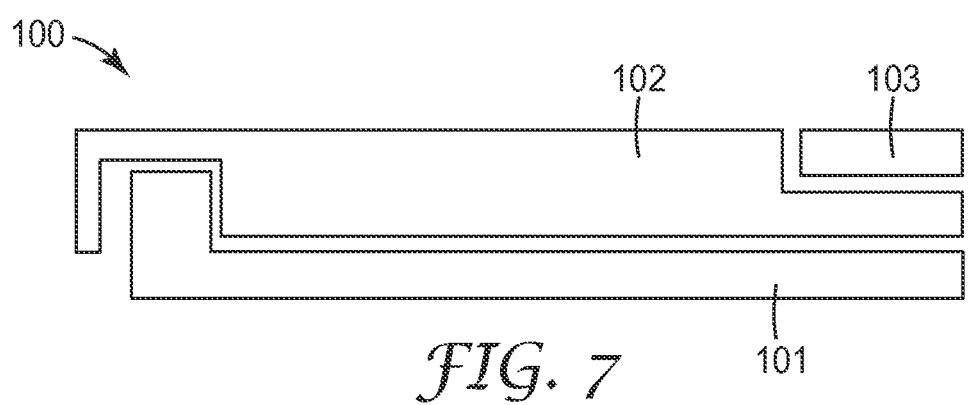

FIGS. 5 to 7 illustrate other embodiments of the electrochemical biosensor electrode strip according to the present invention.

The electrochemical biosensor electrode strip illustrated in FIGS. 5 and 6 is a basic electrode strip, which only comprises the working electrode (101) and the reference electrode (102).

The electrochemical biosensor electrode strip illustrated in FIG. 7 is an electrode strip, which comprises the recognition electrode (103), in addition to the working electrode (101) and the reference electrode (102).

Figure 8:
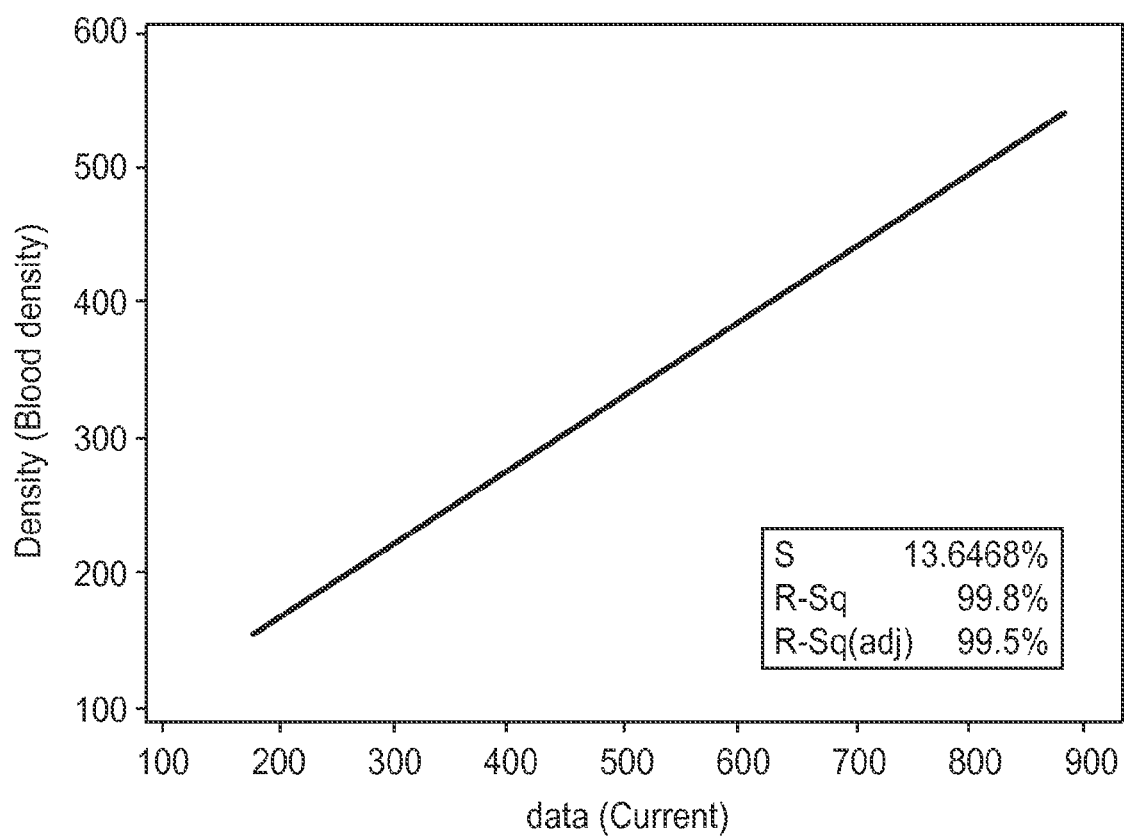
FIG. 8 is a graph showing test results for the electrochemical biosensor electrode strip according to an aspect of the present invention.

FIG. 8 shows a graph of test results for the electrode strip fabricated according to an aspect of the present invention.

The test was conducted by applying voltage of a single digit mV to the electrode and reacting the electrode with a reagent forced to be loaded on the electrode to measure a value of current generated during this process. That is, a current value means concentration of a certain reagent contained in a solution, and it should be verified whether a required quantity of electrons generated in a required quantity of the reagent are properly delivered through the electrode surface. Thus, if the electrode surface and the resistance are uniformed and constant, a constantly linear result value in each electrode as shown in FIG. 8 can be obtained.

The invention claimed is:

1. An electrochemical biosensor electrode strip comprising a non-conductive substrate, and at least two electrodes formed on the substrate and operating as a working electrode and a reference electrode,
wherein the electrodes comprise a carbon layer and a metal layer,
in which the carbon layer is formed directly on the substrate, and the metal layer is formed directly on the carbon layer, the metal layer substantially completely covering the carbon layer,
and the metal layer contains titanium.

2. The electrochemical biosensor electrode strip claimed in claim 1, wherein the carbon layer and the metal layer are formed by sputtering.

3. The electrochemical biosensor electrode strip claimed in claim 1, wherein a thickness of the carbon layer is 1000 Å~1500 Å.

4. The electrochemical biosensor electrode strip claimed in claim 1, wherein a thickness of the metal layer is 500 Å~1500 Å.

5. The electrochemical biosensor electrode strip claimed in claim 1, wherein the non-conductive substrate is an insulating polymer film.

6. The electrochemical biosensor electrode strip claimed in claim 1, wherein the electrochemical biosensor electrode strip further comprises at least one electrode selected from a recognition electrode and an auxiliary electrode.

7. A method of fabricating an electrochemical biosensor electrode strip comprising: preparing a non-conductive substrate; forming a carbon layer directly on the substrate; forming a metal layer containing titanium directly on the formed carbon layer to form a conductive layer consisting of the carbon layer and the metal layer, the metal layer substantially completely covering the carbon layer; and partially etching the conductive layer to pattern at least a working electrode and a reference electrode.

8. The method of fabricating an electrochemical biosensor electrode strip claimed in claim 7, wherein the carbon layer and the metal layer containing titanium are formed by sputtering.

9. The method of fabricating an electrochemical biosensor electrode strip claimed in claim 8, wherein the sputtering is performed in a same chamber.

10. The method of fabricating an electrochemical biosensor electrode strip claimed in claim 7, wherein a thickness of the carbon layer is 1000 Å~1500 Å.

11. The method of fabricating an electrochemical biosensor electrode strip claimed in claim 7, wherein a thickness of the metal layer containing titanium is 500 Å~1500 Å.

12. The method of fabricating an electrochemical biosensor electrode strip claimed in claim 7, wherein the etching is performed by using LASER.

13. The method of fabricating an electrochemical biosensor electrode strip claimed in claim 7, wherein in addition to the working electrode and the reference electrode, at least one selected from an auxiliary electrode and a recognition electrode is further formed.

* * * * *